US 008566124B2

(12) United States Patent
Murawski (10) Patent No.: US 8,566,124 B2
(45) Date of Patent: *Oct. 22, 2013

(54) TEMPLATE BASED FILTERING AND SUMMATIONS FLOW SHEET (71) Applicant: General Electric Company, Schenectady, NY (US)

(72) Inventor: David Murawski, Cary, IL (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/781,101

(22) Filed: Feb. 28, 2013

(65) Prior Publication Data
US 2013/0179765 A1 Jul. 11, 2013

Related U.S. Application Data (63) Continuation of application No. 12/363,161, filed on Jan. 30, 2009, now Pat. No. 8,412,543.

(51) Int. Cl.
G06F 19/00 (2011.01)

(52) U.S. Cl.
USPC ...... 705/3; 705/2; 710/52; 715/214; 715/209; 715/764

(58) Field of Classification Search
USPC .............. 705/2, 3; 710/52; 715/209, 214, 764
See application file for complete search history.

(56) References Cited

U.S. PATENT DOCUMENTS

| | | | |
|---|---|---|---|
| 5,546,580 A | 8/1996 | Seliger et al. | |
| 5,592,945 A | 1/1997 | Fiedler | |
| 5,682,526 A * | 10/1997 | Smokoff et al. | 1/1 |
| 5,950,168 A * | 9/1999 | Simborg et al. | 705/3 |
| 6,115,759 A * | 9/2000 | Sugimura et al. | 710/52 |
| 6,322,502 B1 | 11/2001 | Schoenberg et al. | |
| 6,401,072 B1 * | 6/2002 | Haudenschild et al. | 705/3 |
| 7,374,535 B2 | 5/2008 | Schoenberg et al. | |
| 7,904,822 B2 * | 3/2011 | Monteleone et al. | 715/764 |
| 2002/0138512 A1 * | 9/2002 | Buresh et al. | 707/507 |
| 2004/0024615 A1 | 2/2004 | Monteleone et al. | |
| 2006/0174189 A1 * | 8/2006 | Weitzman et al. | 715/503 |
| 2007/0165049 A1 | 7/2007 | Murawski et al. | |
| 2007/0192134 A1 * | 8/2007 | Littenberg et al. | 705/2 |
| 2010/0198617 A1 | 8/2010 | Murawski et al. | |

OTHER PUBLICATIONS

Google search, Nov. 27, 2012.*
Google patents search, Jun. 10, 2013.*
Google search results, Nov. 27, 2011.

(Continued)

Primary Examiner — Dilek B Cobanoglu
(74) Attorney, Agent, or Firm — Hanley, Flight and Zimmerman, LLC (57) ABSTRACT Systems and methods are disclosed to provide a moveable summary column and/or row for an electronic medical flow sheet. The summary column and/or row can provide various summations of the patient's data records for any time period depending on where the moveable summation column and/or row is placed. The summation of the various patient data depends on a selected type of patient data. The summary column and/or row can be moved by the user to any spot in the patient data portion of the medical flow sheet to sum up different intervals of data. The moveable summation column and/or row presents summary data for patient parameters depending on the placement of the summation column and/or row.

20 Claims, 5 Drawing Sheets (56) References Cited

OTHER PUBLICATIONS

Google Patents search results, Nov. 27, 2011.
United States Patent and Trademark Office, "Notice of Allowance," issued in connection with U.S. Appl. No. 12/363,161, mailed on Nov. 30, 2012, 18 pages.
United States Patent and Trademark Office, "Final Office Action," issued in connection with U.S. Appl. No. 12/363,161, mailed on Oct. 20, 2011, 11 pages.
United States Patent and Trademark Office, "Non-Final Office Action," issued in connection with U.S. Appl. No. 12/363,161, mailed on Apr. 1, 2011, 14 pages.

* cited by examiner

TEMPLATE BASED FILTERING AND SUMMATIONS FLOW SHEET

RELATED APPLICATIONS

This patent claims the benefit of priority as a continuation of U.S. patent application Ser. No. 12/363,161, filed on Jan. 30, 2009, entitled "Template Based Filtering and Summations Flowsheet", which is herein incorporated by reference in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The presently described technology generally relates patient information management. More specifically, the present technology relates to the organization and display of various kinds of medical data.

Tremendous amounts of medical data relating to patient treatment and patient management information related to insurance, billing and the like are generated and maintained in the routine practice of medicine. Historically, a paper based system was used to record this information in what was called patient flow sheets. As more and more data became available and required, computerized flow sheets were developed to record and maintain this data. Computer based flow sheets allow a dynamic view of the patient's medical history The existing electronic based flow sheets usually record such exemplary values as vital signs (i.e., blood pressure, temperature heart rate and the like), fluid intake and output information and many other parameters. Other exemplary flows sheets may be for the pharmacy and laboratory results. Additionally, certain flow sheets may be restricted to doctors, pharmacists or nurses. Flow sheets are usually template based and the administration of each facility can tailor the flow sheet to their particular needs and practices. Generally, the existing flow sheets have summation columns that constrain the user to view only the summation totals at a predetermined time interval, such as end of work shifts. This lack of flexibility of the summation columns limits the use of flow sheets and limits the user's use of information in the flow sheet.

Thus, a need exists for a flexible system and method to optimize the information provided to the practitioner to support the practitioner's care of the patient. More flexible display of summation information in the flow sheet will result in faster recognition of a trend and thus will ultimately lead to better patient care.

BRIEF SUMMARY OF THE INVENTION

Certain embodiments of the present technology include an electronic medical flow sheet system comprising, a flow sheet application component, a flow sheet summation component, and a user interface adapted to receive an image from a database.

Certain embodiments of the present technology provide a method of receiving patient data into a database comprising, selecting a patient, selecting a type of electronic flow sheet, transmitting, transmitting patient data to an electronic flow sheet generator, displaying an image generated by the electronic selected electronic flow sheet at a user interface, positioning a moveable summation column over a selected patient data column, and displaying summation data in the moveable summation column in the electronic flow sheet at the user interface Certain embodiments of the present technology provide a computer-readable medium including a set of instructions for execution on a computer, the set of instructions including a electronic flow sheet routine adapted to display a electronic medical flow sheet to a user, a moveable summation column routine capable of producing a summation of a patient's data depending on a placement of the moveable summation column.

The foregoing summary, as well as the following detailed description of certain embodiments of the present technology, will be better understood when read in conjunction with the appended drawings. For the purpose of illustrating the technology, certain embodiments are shown in the drawings. It should be understood, however, that the present invention is not limited to the arrangements and instrumentality shown in the attached drawings.

DETAILED DESCRIPTION OF THE INVENTION

As illustrated in the drawings, the template base filtering and summations flowsheet is designed particularly for use in template based flow sheets to specify summation requirements for each row in the flow sheet and provide a moveable column that summarizes data based on the individual row's summation criteria.

Figure 1:
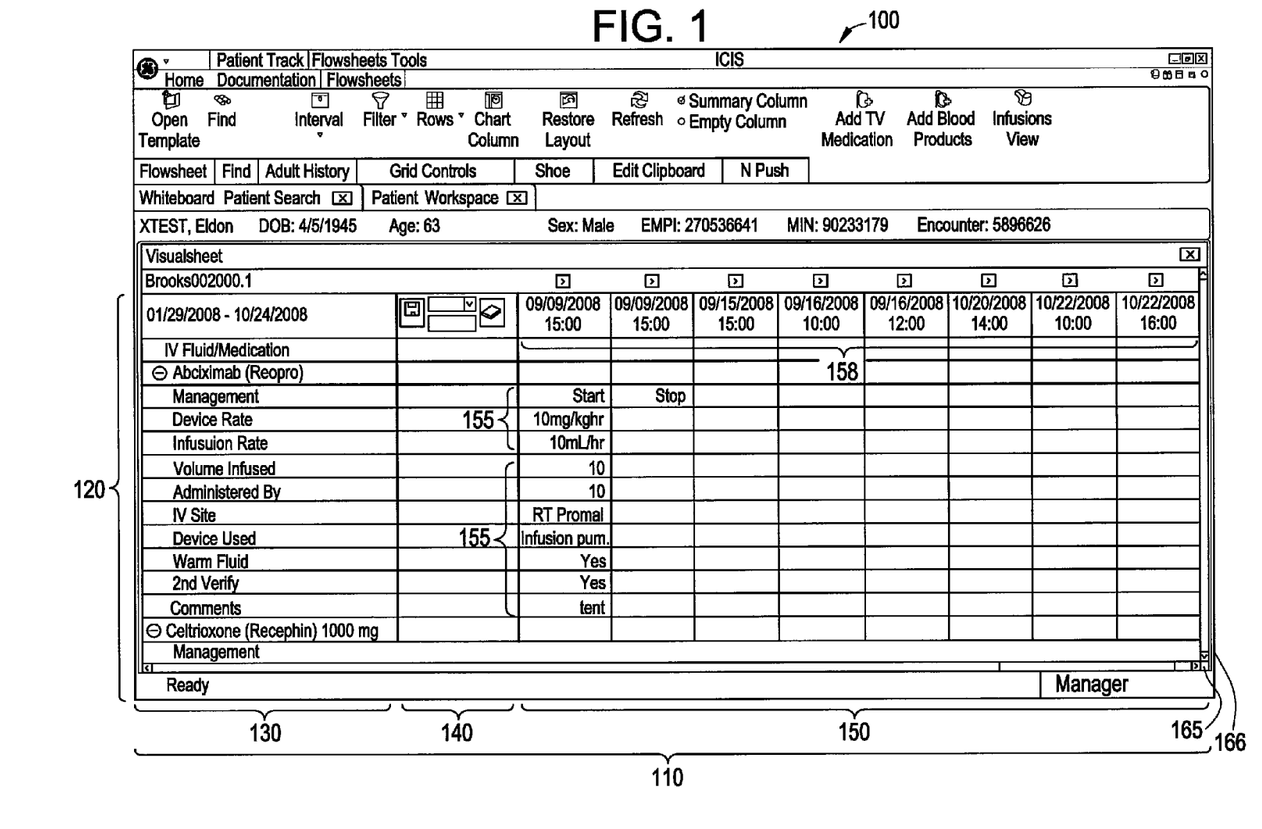
FIG. 1 is an exemplary user interface of a patient flow sheet.

FIG. 1 illustrates a typical flow sheet 100 for an individual patient. The flow sheet provides a concise view of selected patient information for a given time period. The medical flow sheet consists of a number of columns 110 and a number of rows 120. A left most column 130 typically lists various patient parameters to be entered into the rows 120 of the medical flow sheet. These parameters may be vital sign information, treatments provided, medicine dispensed laboratory results, etc. To the right of column 130 is column 140 which is a blank column for entering data. To the right of column 140, are a number of columns 150 which contain parameter values 155 gathered at a specific time and date 158. The date and time 158 of each column 150 are indicated along the top of columns 150. Date and time 158 are variable and may be set by the user. Each row in columns 150 may contain data corresponding to the different row parameters in column 130. Generally, columns 150 are ordered according to time and date. As can be contemplated, only a portion of the information may be displayed on a display device at any given time. Arrows 165 and 166 permit flow sheet 100 to be scrolled up, down, left, and right. Further, a variety of different flow sheets with different arrangement of parameters in column 130 may be constructed depending on the application.

The flow sheet 100 discussed above is know in the art. The preferred embodiment of the present technology improves on the flow sheet discussed above.

Figure 2:
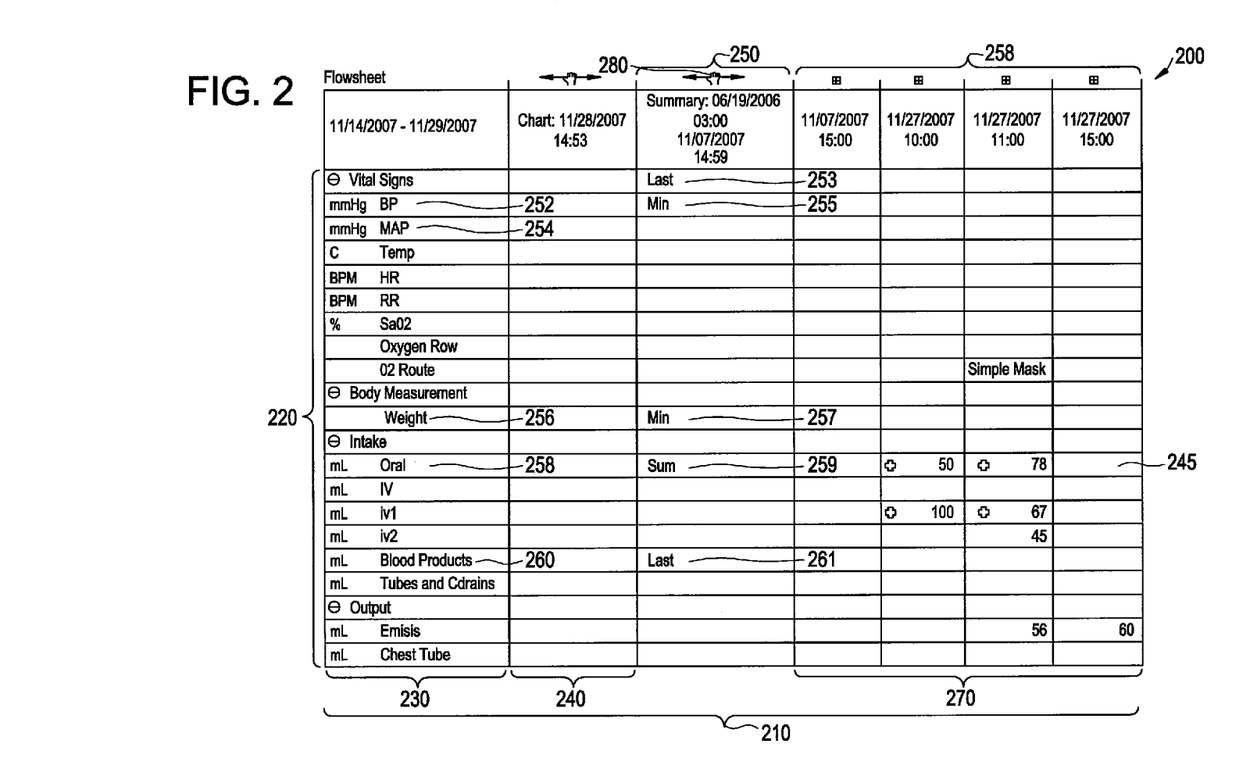
FIG. 2 illustrates an exemplary flow sheet with a summation column in accordance with an embodiment of the present technology.
Figure 3:
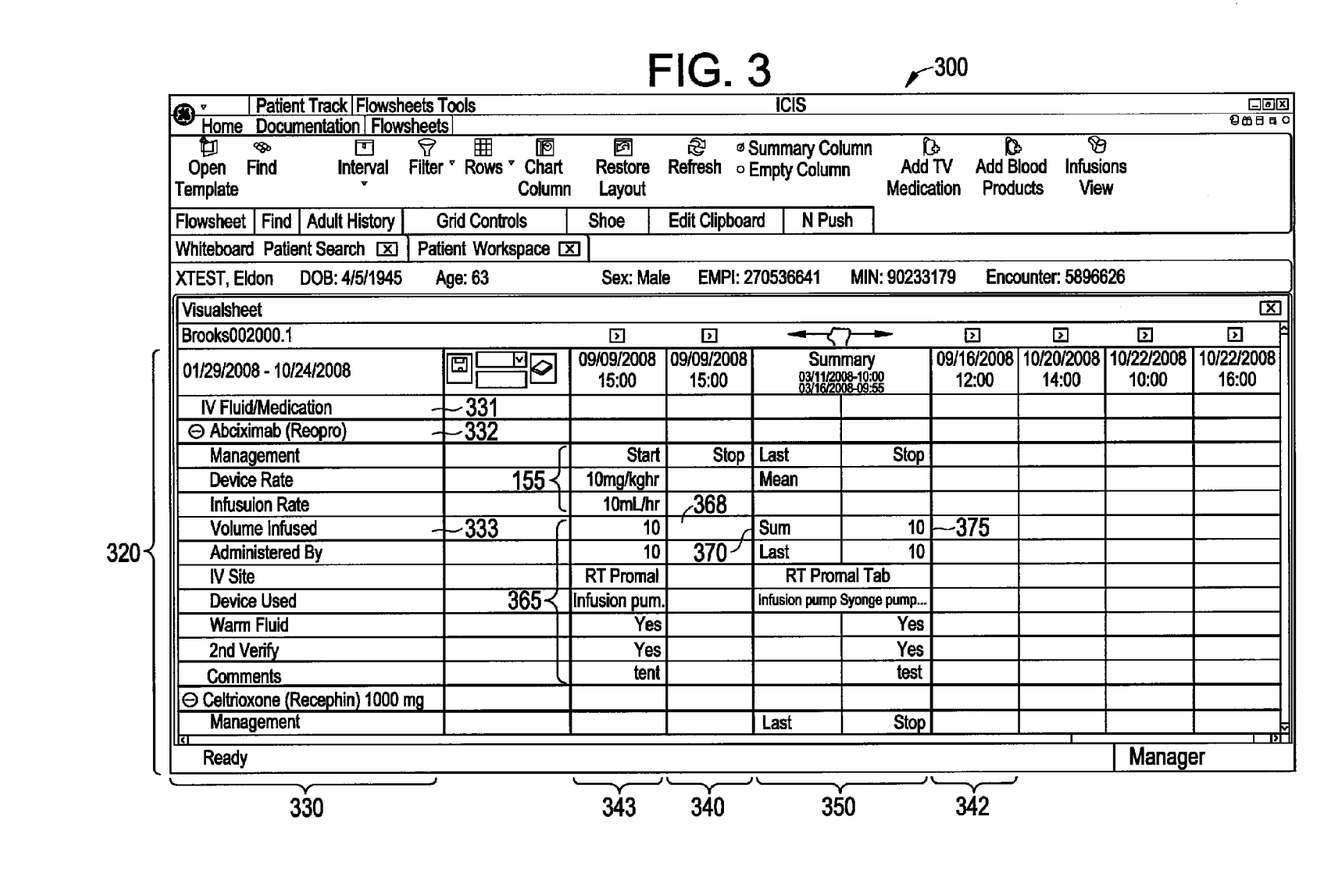
FIG. 3 illustrates an exemplary flow sheet with a summation column containing patient parameter values in accordance with an embodiment of the present technology.

FIG. 2 Illustrates a template based flow sheet 200 that is similar to flow sheet 100 in FIG. 3 with the addition of a moveable summation column 250 in accordance with an aspect of the present technology. The medical flow sheet 200 consists of a number of columns 210 and a number of rows 220. A left most column 230 typically lists various patient parameters to be entered into the rows 220 of the medical flow sheet. To the right of column 230 is data entry column 240 which is a blank column for entering data. To the right of data entry column 240, are a number of data columns 270 which contain parameter values 245 gathered at a specific time and date 258. The date and time 258 of each data column 270 are indicated along the top of data columns 270. Date and time 258 are variable and may be set by the user. Each row in data columns 270 may contain data corresponding to the different row parameters in column 230. Generally, data columns 270 are ordered according to time and date. As can be contemplated, only a portion of the information may be displayed on a display device at any given time.

As indicated in FIG. 2, a summary column 250 is displayed. Summary column 250 is configurable to specify summation criteria for each selected row 220. Typically, administrators create templates that define the structure of the flow sheet. When developing the parameters for the particular flow sheet, administrators can create templates that define different arrangements of data in column 230. Additionally, the administrators can specify summation criteria for column 250 for each row 220 in the flow sheet 200. Examples of row summary properties are total for the time period selected, the highest value in the time period, the lowest value in the time period, the range of values, the average of values, the last value entered first value entered and the sum of the values entered. The selection of the type of summation desired depends on the row parameter. For example, in FIG. 2, BP 252 or blood pressure has a unit of measure of mmHg. In FIG. 3, the summation row property for this parameter is "Last" 253. Other exemplary summation row properties depicted in FIG. 2 are "Min" 255 for parameter MAP 254, "Min" 257 for parameter Weight 256, "Sum" 259 for parameter Oral 258, and "Last" 261 for Parameter Blood Products 260. The particular summation criteria is determined by the administrators who develop the template based flow sheet. As indicated by symbol 280, summation column 250 is moveable by clicking on symbol 280 and dragging summation column 250 to a user desired location on flow sheet. The time range of which data is applied to the summation column 250 to summarize data can be determined by where the user places the summation column 250 amongst data columns 270

FIG. 3 Illustrates a medical flow sheet 300 with a template based moveable summation column 350 containing summation criteria for each row and summation values in accordance with an aspect of the present technology. As indicated in FIG. 3, moveable summation column 350 has been dragged and dropped in between data columns 340 and 342. The time range of which data is applied to summation column 350 is determined by where the user places the summation column 350. In FIG. 3, moveable summation column 350 has various summation criteria depending on the individual row's parameter. Where patient information is found at the intersection of a row and column, the flow sheet indicates that the recorded information was obtained at the date and time or during the period of time specified for the indicated column. For example, in column 330, under the heading of IV Fluid/Medication 331, the drug Abciximab is listed in row 332. Under the drug Abciximab, certain parameters have been listed. One of the parameters under Abciximab 332 is row 333 "Volume Infused." Turning to data column 343, the specific date and time of column 343 is Sep. 9, 2008 at 15:00 hrs 360. Column 343 contains certain patient data 365 obtained and entered into the medical flow sheet 300 for the specific date and time. Particularly, where row 333 containing the parameter of Volume Infused, intersects column 343, the patient data 368 of 10 is found. Now turning to the moveable summation column 343, the desired summation criteria for this row parameter 333 is Sum 370. As can be seen from the FIG. 3, various summation criteria may be defined when the flow sheet is created. Looking at the right hand portion of summation column 350 for the summation criteria of "Sum" 370, a summation value 375 of 10 for the time interval of at the top of summation column 350. This time interval is usually based on a specific visit or encounter by the patient to the medical facility, but can be modified by the user. With the moveable summation column described above, summation of any type for any interval can be obtained by the user.

Figure 4:
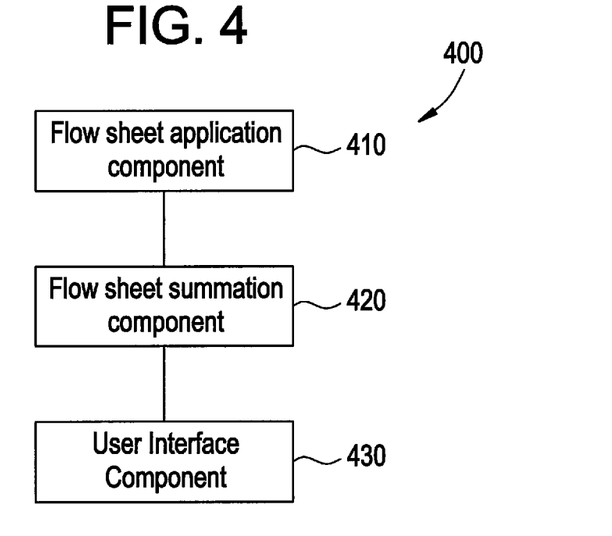
FIG. 4 illustrates a system for a medical flow sheet with a floating summation column according to an embodiment of the present technology.

FIG. 4 illustrates generally a block diagram 400 of the template base filtering and summations system. The system 400 includes a flow sheet application component 410, a flow sheet summation component 420, and a flow sheet component 430.

The flow sheet application component 410 may be in communication with a database which contains data about a patient received from a variety of sources, such as manual input and various diagnostic components. Particular data from a database may be sent to the flow sheet application component 410 so that the user, such as a nurse or physician, can view the patient's data. It is contemplated that the user may have different interests of the patient's data depending on their job function. For example a physician may be interested in a certain set of data and a nurse may be interested in another set of data.

After the user selects the type of patient data to be displayed, it is contemplated that a summation column particular to that data will also be displayed produced by the summation column component 420. The summation column component 420 may have different parameters for summation depending on the particular data set that the user selects. The summation column component can be dragged and dropped into any location on the flow sheet contain patient data to summarize the data.

After the user sects the desired type patient data, a flow sheet 430 is displayed from the flow sheet application component 410 and the flow sheet summation component 420. It is contemplated that the flow sheet with a moveable summation column of the present technology can be adapted for a particular user to display different data subsets such as vital signs, drug data, hematology.

Figure 5:
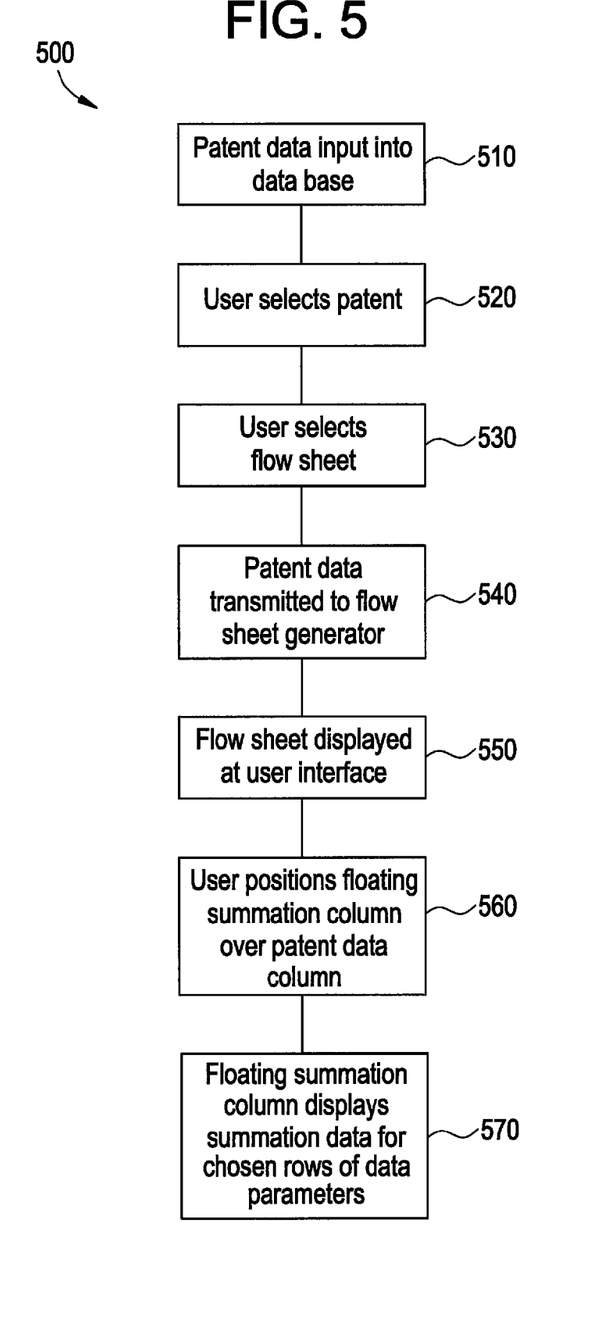
FIG. 5 illustrates a flow diagram for a method for displaying a medical flow sheet with a floating summation column according to an embodiment of the present technology.

FIG. 5 illustrates a flow diagram 500 for a method for displaying a medical flow sheet with a floating summation column according to an embodiment of the present technology. The method includes the following steps. At step 510, patient data is entered into a database. At step 720, a user selects a patient for which a medical flow sheet is to be displayed. At step 530, a user selects the particular flow sheet to be displayed for the selected patient. At step 540, data from the data base is transmitted to a flow sheet generator. At step 550, a flow sheet is displayed at the user interface. At step 560, the user positions the floating summation column over patient data column. At step 570, the floating summation column displays summation data for designated rows in accordance with certain summation criteria.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

One or more of the steps of the method may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Several embodiments are described above with reference to drawings. These drawings illustrate certain details of specific embodiments that implement the systems and methods and programs of the present invention. However, describing the invention with drawings should not be construed as imposing on the invention any limitations associated with features shown in the drawings. The present invention contemplates methods, systems, and program products on any machine-readable media for accomplishing its operations. As noted above, the embodiments of the present invention may be implemented using an existing computer processor, or by a special purpose computer processor incorporated for this or another purpose or by a hardwired system.

As noted above, certain embodiments within the scope of the present invention include program products comprising machine-readable media for carrying or having machine-executable instructions or data structures stored thereon. Such machine-readable media can be any available media that can be accessed by a general purpose or special purpose computer or other machine with a processor. By way of example, such machine-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Certain embodiments of the invention are described in the general context of method steps which may be implemented in one embodiment by a program product including machine-executable instructions, such as program code, for example in the form of program modules executed by machines in networked environments. Generally, program modules include routines, programs, objects, components, data structures, etc., that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

Certain embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hard-wired links, wireless links, or by a combination of hardwired or wireless links) through a communications network. In a distributed computing environment, program modules may be located in both local and remote memory storage devices.

An exemplary system for implementing the overall system or portions of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD-ROM or other optical media. The drives and their associated machine-readable media provide nonvolatile storage of machine-executable instructions, data structures, program modules and other data for the computer.

The foregoing description of embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principals of the invention and its practical application to enable one skilled in the art to utilize the invention in various embodiments and with various modifications as are suited to the particular use contemplated.

Those skilled in the art will appreciate that the embodiments disclosed herein may be applied to the formation of any healthcare information system. Certain features of the embodiments of the claimed subject matter have been illustrated as described herein; however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A computer-implemented method to display an electronic medical flow sheet with a moveable summation area, the method comprising:
   selecting a type of patient data to be displayed;
   displaying, via a user interface, the selected type of patient data in an electronic medical flow sheet, information in the electronic medical flow sheet organized according to at least one of columns and rows;
   providing at least one of a moveable summation column and a moveable summation row particular to the selected type of patient data, the moveable summation column or moveable summation row displayed in conjunction with the electronic medical flow sheet, the moveable summation column or moveable summation row to be positioned by a user over a particular column or a particular row of the electronic medical flow sheet to provide summation data for the particular row or the particular column according to the electronic medical flow sheet and selected type of patient data; and
   displaying summation data in the at least one of moveable summation column and moveable summation row in conjunction with the electronic medical flow sheet via the user interface.

2. The method of claim 1, wherein the electronic medical flow sheet is presented in a column form and wherein a plurality of patient information columns contain a medical record for a medical event for a selected patient associated with a time and a date.

3. The method of claim 1, wherein the electronic medical flow sheet is presented in a column form and wherein a medical parameter column in the electronic medical flow sheet contains a plurality of medical data parameters.

4. The method of claim 1, wherein the moveable summation column summarizes data based on a row in the moveable summation column.

5. The method of claim 1, wherein the moveable summation row summarizes data based on a column in the moveable summation row.

6. The method of claim 1, wherein a type of the electronic medical flow sheet is associated with a set of medical event parameters for a particular medical team member.

7. The method of claim 6, wherein the medical team member is selected from the group consisting of doctor, nurse, pharmacist, administrator, insurance coordinator.

8. The method of claim 1, wherein an interval for the summation data of the moveable summation column or the moveable summation row is automatically determined based on where a user places the moveable summation column or the moveable summation row in the electronic medical flow sheet.

9. The method of claim 8, wherein the interval for the summation data of the moveable summation column or the moveable summation row is configurable by a user.

10. A non-transitory computer-readable storage medium including a set of instructions for execution on a computer, the set of instructions when executed configuring the computer to implement a method, the method comprising:
    selecting a type of patient data to be displayed;
    displaying, via a user interface, the selected type of patient data in an electronic medical flow sheet, information in the electronic medical flow sheet organized according to at least one of columns and rows;
    providing at least one of a moveable summation column and a moveable summation row particular to the selected type of patient data, the moveable summation column or moveable summation row displayed in conjunction with the electronic medical flow sheet, the moveable summation column or moveable summation row to be positioned by a user over a particular column or a particular row of the electronic medical flow sheet to provide summation data for the particular row or the particular column according to the electronic medical flow sheet and selected type of patient data; and
    displaying summation data in the at least one of moveable summation column and moveable summation row in conjunction with the electronic medical flow sheet via the user interface.

11. The computer-readable storage medium of claim 10, wherein the electronic medical flow sheet is presented in a column form and wherein a plurality of patient information columns contain a medical record for a medical event for a selected patient associated with a time and a date.

12. The computer-readable storage medium of claim 10, wherein the electronic medical flow sheet is presented in a column form and wherein a medical parameter column in the electronic medical flow sheet contains a plurality of medical data parameters.

13. The computer-readable storage medium of claim 10, wherein the moveable summation column summarizes data based on a row in the moveable summation column.

14. The computer-readable storage medium of claim 10, wherein the moveable summation row summarizes data based on a column in the moveable summation row.

15. The computer-readable storage medium of claim 10, wherein a type of the electronic medical flow sheet is associated with a set of medical event parameters for a particular medical team member.

16. The computer-readable storage medium of claim 15, wherein the medical team member is selected from the group consisting of doctor, nurse, pharmacist, administrator, insurance coordinator.

17. The computer-readable storage medium of claim 10, wherein an interval for the summation data of the moveable summation column or the moveable summation row is automatically determined based on where a user places the moveable summation column or the moveable summation row in the electronic medical flow sheet.

18. The computer-readable storage medium of claim 17, wherein the interval for the summation data of the moveable summation column or the moveable summation row is configurable by a user.

19. An electronic medical flow sheet system comprising:
    a processor and a memory configured to generate and provide an electronic medical flow sheet via a graphical user interface, the processor configured to:
    facilitate selection of a type of patient data to be displayed;
    display, via the graphical user interface, the selected type of patient data in the electronic medical flow sheet, information in the electronic medical flow sheet organized according to at least one of columns and rows;

provide at least one of a moveable summation column and a moveable summation row particular to the selected type of patient data, the moveable summation column or moveable summation row displayed in conjunction with the electronic medical flow sheet, the moveable summation column or moveable summation row to be positioned by a user over a particular column or a particular row of the electronic medical flow sheet to provide summation data for the particular row or the particular column according to the electronic medical flow sheet and selected type of patient data; and display summation data in the at least one of moveable summation column and moveable summation row in conjunction with the electronic medical flow sheet via the user interface.

20. The system of claim 19, wherein, if the moveable summation column is provided, the processor is to summarize data in the moveable summation column based on a row in the moveable summation column, and wherein, if the moveable summation row is provided, the processor is to summarize data based on a column in the moveable summation row.

* * * * *